(12) United States Patent
Al-Obeidi et al.

(10) Patent No.: US 6,676,905 B2
(45) Date of Patent: Jan. 13, 2004

(54) MULTI-WELL PLATE WITH PERIMETERAL HEAT RESERVOIR

(75) Inventors: Fahad A. D. Al-Obeidi, Tucson, AZ (US); Richard E. Austin, Oro Valley, AZ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/875,999

(22) Filed: Jun. 7, 2001

(65) Prior Publication Data

US 2002/0187078 A1 Dec. 12, 2002

(51) Int. Cl.[7] .................................................. B01L 3/00
(52) U.S. Cl. ........................ 422/102; 422/99; 219/428; 435/288.4; 435/288.5; 435/305.2
(58) Field of Search ..................... 422/104, 99, 102; 435/288.2, 288.3, 288.4, 288.5, 305.1, 305.2; 219/428

(56) References Cited

U.S. PATENT DOCUMENTS

| | | | |
|---|---|---|---|
| 3,211,531 A | * 10/1965 | Benzinger | 422/51 |
| 3,245,758 A | * 4/1966 | Benzinger et al. | 436/147 |
| 3,273,968 A | * 9/1966 | Benzinger | 422/51 |
| 4,657,867 A | * 4/1987 | Guhl et al. | 435/305.3 |
| 4,673,651 A | * 6/1987 | Rothenberg et al. | 220/23.8 |
| 4,786,601 A | * 11/1988 | Rothenberg | 422/942 |
| 5,255,976 A | * 10/1993 | Connelly | 374/31 |
| 5,451,524 A | 9/1995 | Coble et al. | 435/301 |
| 5,609,826 A | * 3/1997 | Cargill et al. | 422/101 |
| 5,716,584 A | * 2/1998 | Baker et al. | 422/131 |
| 5,725,835 A | * 3/1998 | Lautenschlager | 422/129 |
| 5,746,982 A | 5/1998 | Saneii et al. | 422/134 |
| 5,866,342 A | 2/1999 | Antonenko et al. | 435/7.1 |
| 5,932,075 A | * 8/1999 | Strauss et al. | 204/157.15 |
| 6,086,831 A | 7/2000 | Harness et al. | 422/199 |
| 6,120,741 A | * 9/2000 | Jacquault et al. | 422/199 |
| 6,126,904 A | 10/2000 | Zuellig et al. | 422/130 |
| 6,238,627 B1 | * 5/2001 | McGowan et al. | 422/101 |
| 6,423,948 B1 | * 7/2002 | Kwasnoski et al. | 219/428 |

FOREIGN PATENT DOCUMENTS

| | | | | |
|---|---|---|---|---|
| WO | WO 99/54031 | 10/1999 | | B01J/19/00 |
| WO | WO 00/09255 | 2/2000 | | B01J/19/00 |
| WO | WO 00/26096 | 5/2000 | | B65D/1/36 |

* cited by examiner

Primary Examiner—Jill Warden
Assistant Examiner—Elizabeth Quan
(74) Attorney, Agent, or Firm—Synnestvedt & Lechner LLP

(57) ABSTRACT

A multi-well plate is disclosed for holding chemical compounds for heating in a microwave oven. The plate is a substantially planar member having wells arranged in an array of rows and columns in its upper surface. The plate has heat reservoirs in the form of fluid filled channels or elongated solid bodies positioned lengthwise along the side portions of the plate to reduce temperature gradients among the wells across the length and width of the plate. The heat reservoirs prevent or mitigate heat loss from the wells near the side portions of the plate and ensure that the compounds in all of the wells have a uniform temperature.

25 Claims, 6 Drawing Sheets

MULTI-WELL PLATE WITH PERIMETERAL HEAT RESERVOIR

FIELD OF THE INVENTION

This invention concerns multi-well plates for organic chemical synthesis testing, and especially to multi-well plates useable in a microwave.

BACKGROUND OF THE INVENTION

Organic chemical synthesis concerns the chemistry of the compounds of carbon and is fundamental to a broad range of industrial and research activities, notably pharmaceuticals, but also including polymer chemistry, the chemistry of food additives, flavor chemistry, as well as biochemistry.

Synthesis testing involves the determination of percentage yield of product from starting reagents. Synthesis testing may be performed in either the solid or liquid phases and is conveniently accomplished using a multi-well plate, wherein reagents of various concentrations in each well are permitted to react and form product compounds. The percentage yield for the various starting concentrations is measured and compared to determine the optimum reagent ratios which will yield the largest percentage of product.

When the reaction is endothermic or when heat is a catalyst, it is convenient to heat the reagents in a microwave oven. Microwave heating works by exciting molecules having a dipole moment at or near the resonant frequency of the dipole and, hence, is very selective in what is heated within the oven. For example, the microwaves bombarding a multi-well plate will heat the reagents within the wells but will not heat the plate or the air within the oven. While this is economical, because energy is not wasted heating items other than the constituents, there is a drawback in that temperature differences are present between items within the oven, such as between the reagents and the plate, as well as between the plate and the ambient air. Such temperature differences inevitably cause heat transfer to occur. For example, heat is transferred from the reagents to the plate and from the plate to the ambient air within the microwave chamber. The heat transfer leads to transient and static temperature gradients across the plate. Relatively lower temperatures are found in the wells near the edges of the plate where the heat transfer from the plate to the air is greatest due to the relatively large surface area of the side portions of the plate in contact with the air. Relatively higher temperatures are present in the wells near the center of the plate where the heat transfer is not as great because there is less surface area from which heat is lost.

The temperature gradients cause uneven results to occur, thereby biasing the testing and providing false results since all of the samples are not being tested at the same temperature due to the gradients formed across the plate. There is clearly a need for a multi-well plate useable in a microwave oven which does not suffer from the disadvantages of temperature gradients and which will yield consistent, uniform results in testing.

SUMMARY AND OBJECTS OF THE INVENTION

The invention concerns a multi-well plate for holding a compound for testing. The plate is formed from a substantially planar member having an upper surface and a plurality of side portions bounding the planar member. A plurality of wells are positioned in the planar member and are adapted to hold samples of the compound. Each of the wells has an opening located on the upper surface. A first group of the wells are arranged adjacent to one of the side portions. A first elongated body extends lengthwise along the one side portion adjacent to the first group of wells. The body has a capacity to act as a heat reservoir to resist temperature changes of the samples in the first group of wells relative to the samples in others of the wells. Preferably, the body extends substantially continuously around the planar member and serves as a heat reservoir to resist temperature changes of samples in any other adjacent wells.

In its preferred embodiment, the substantially planar member is bounded by downwardly depending side portions. The first group of wells is arranged adjacent to one of the side portions. The elongated body comprises a first elongated chamber which extends within the plate lengthwise along the one side portion and is positioned between the one side portion and the first group of wells. The first chamber is adapted to contain a fluid which has a capacity to act as a heat reservoir and resist temperature changes of the samples in the first group of wells relative to the samples in others of the wells.

In the preferred embodiment, the first chamber is filled with a liquid and is sealed to isolate it from the ambient. In an alternate embodiment, the chamber is initially air-filled and there is a port in the planar member in fluid communication with the first chamber. The port is adapted to receive the fluid, preferably a liquid which may be poured through the port to fill the first chamber. Preferably, the port is positioned on the upper surface.

The plate preferably has a second group of the wells arranged adjacent to another of the side portions and a second elongated chamber extending within the plate lengthwise along the other side portion. The second chamber is positioned between the other side portion and the second group of wells. Similar to the first chamber, the second chamber is also adapted to contain a fluid having a capacity to act as a heat reservoir and resist temperature changes of the samples in the second group of the wells relative to the samples in others of the wells. Preferably, the first and the second chambers are in fluid communication with each other.

In another embodiment, the elongated body is a solid material which may be heated by the microwaves and preferably extends continuously around the planar member. The solid material may be considered to form the side portions or it may be positioned within the elongated chamber.

It is an object of the invention to provide a multi-well plate suitable for use in a microwave oven.

It is another object of the invention to provide a multi-well plate in which temperature differences between wells is minimized.

It is another object of the invention to reduce or eliminate the presence of temperature gradients across the plate.

These and other objects of the invention will become apparent from consideration of the following drawings and detailed description of preferred embodiments of the invention.

DETAILED DESCRIPTION OF THE PREFERRED EMBODIMENT

Figure 1:
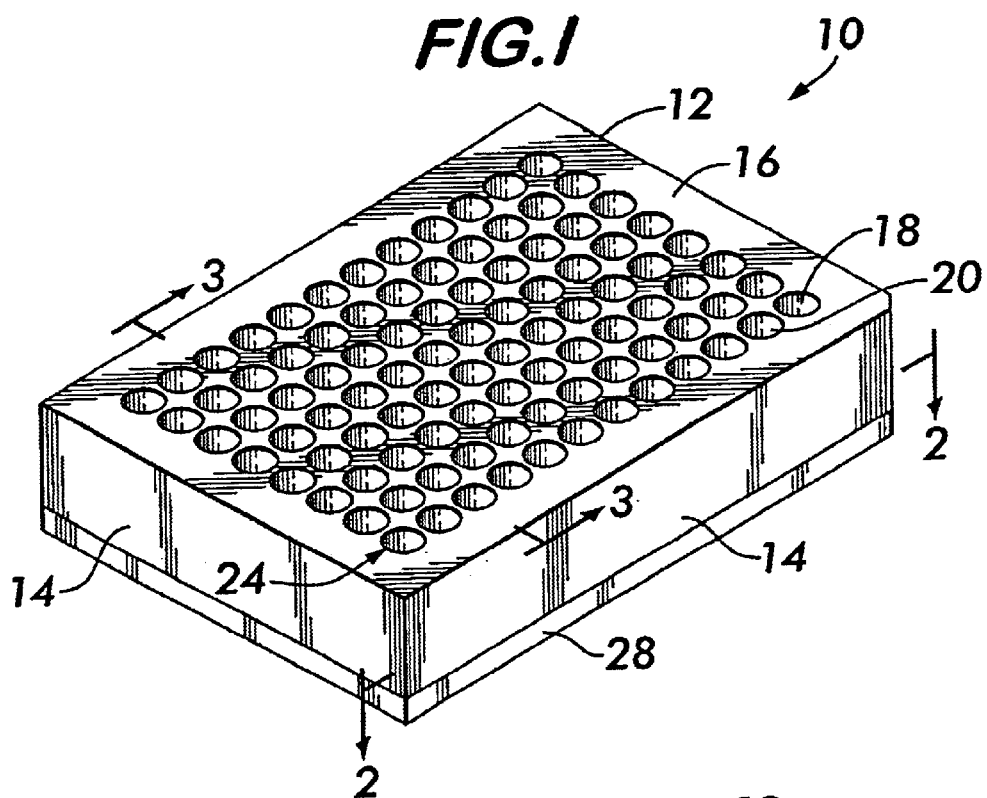
FIG. 1 is a perspective view of a multi-well plate according to the invention.

FIG. 1 shows a multi-well plate 10 according to the invention. Plate 10 is a substantially planar member 12 bounded by downwardly depending side portions 14. The plate has an upper surface 16 and a plurality of wells 18, each well having an opening 20 on the upper surface 16. The wells are preferably arranged in a regular array of rows and columns and are adapted to hold samples of compounds for heating in an experiment, for example, one involving solid phase synthesis.

Figure 2:
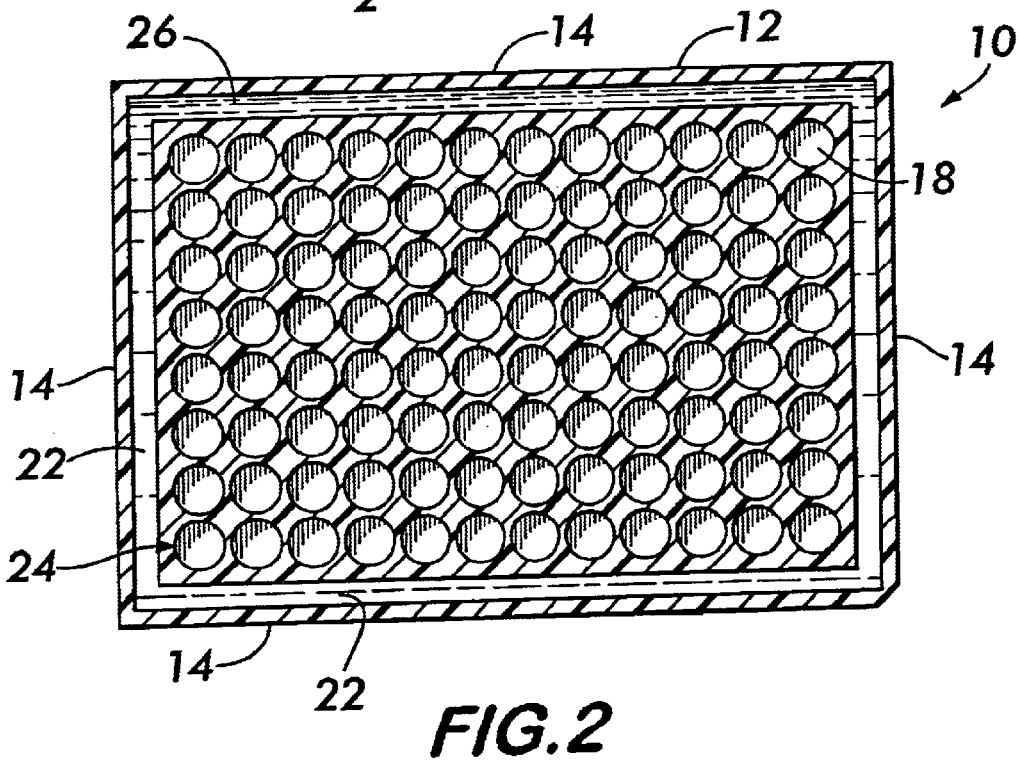
FIG. 2 is a plane sectional view of the plate shown in FIG. 1 taken along lines 2—2.
Figure 3:
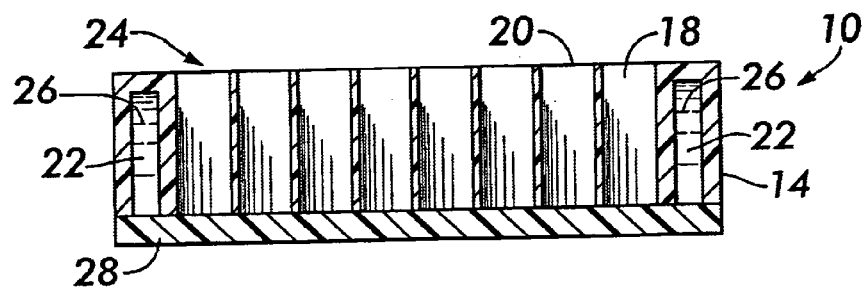
FIG. 3 is a cross-sectional view of the plate shown in FIG. 1 taken along lines 3—3.

As best shown in FIGS. 2 and 3, an elongated chamber 22 extends lengthwise within the planar member 12 between one of the side portions 14 and a row or group of wells 24 proximal to the side portion. In the preferred embodiment, the chamber extends continuously around the entire planar member 12 between the outermost rows of wells and the proximal side portions 14. Preferably, the chamber is permanently sealed and isolated from the ambient and contains a substance 26, which has a capacity to act as a heat reservoir, i.e., the substance is heatable by microwave radiation and has the ability to store and transfer heat. The preferred substance 26 is a liquid and has a higher boiling point than the temperature at which the experiment is designed to run for reasons described below.

The plate illustrated in FIG. 1 is preferably made of polytetrafluoroethylene or another relatively inert substance which is transparent to microwaves (i.e., will not heat up significantly when subjected to microwave radiation), will not react with the compound in the wells and which can withstand relatively high temperatures, at least in excess of the experiment temperature. The plate may be machined from a solid block, the channel filled with the substance 26 and then sealed with the bottom plate 28, attached with adhesives or fasteners or other appropriate means.

Figure 4:
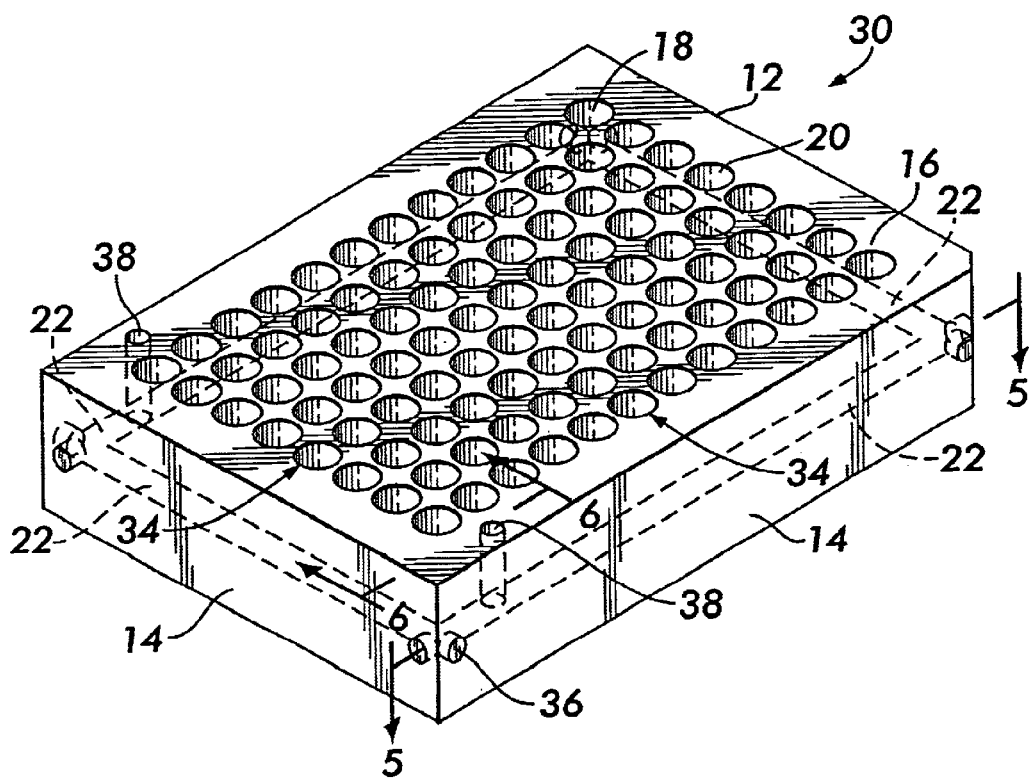
FIG. 4 is a perspective view of another embodiment of a multi-well plate according to the invention.
Figure 5:
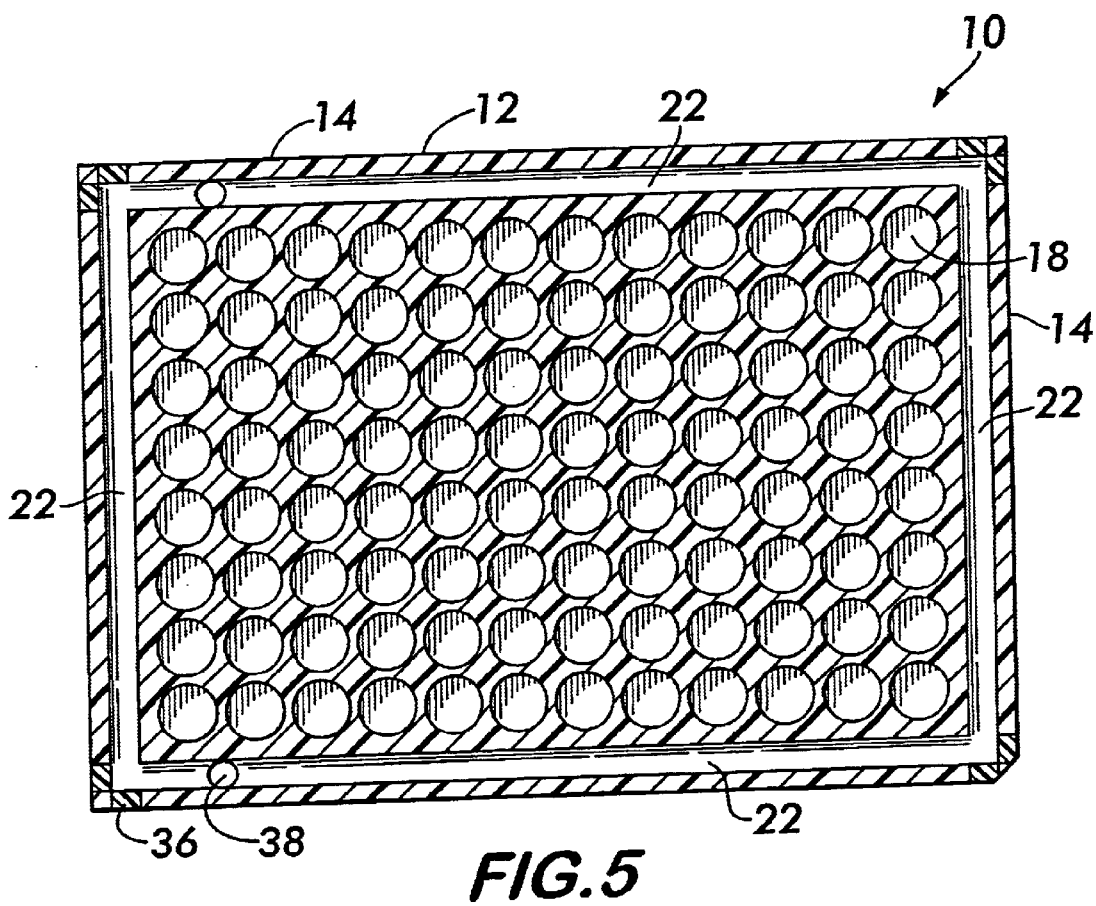
FIG. 5 is a plane sectional view of the multi-well plate shown in FIG. 4 taken along lines 5—5.

FIG. 4 shows another embodiment of a multi-well plate 30 wherein one or more chambers 22 are drilled into the planar member 12, each chamber being positioned between a respective row of wells 34 and a side portion 14. As shown in FIG. 5, chambers 22 preferably surround the entire planar member 12 and are in fluid communication with one another. One or more plugs 36, as necessary, are used to seal the chambers to prevent the fluid contents from escaping. A fill port 38, in fluid communication with a chamber 22, is preferably located on the upper surface 16 of the planar member 12 to permit a liquid to be poured into the chambers.

It is convenient to use two fill ports 38 as shown in FIG. 4, one of the ports allowing air to escape from the chamber or chambers as fluid is poured into the other.

Figure 6:
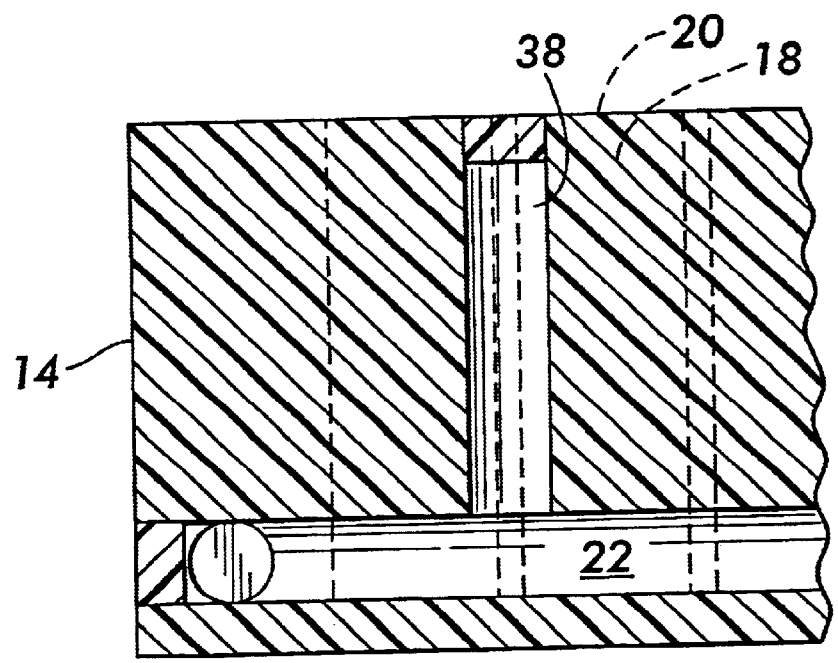
FIG. 6 is a partial cross-sectional view of the multi-well plate taken along lines 6—6 in FIG. 4.
Figure 7:
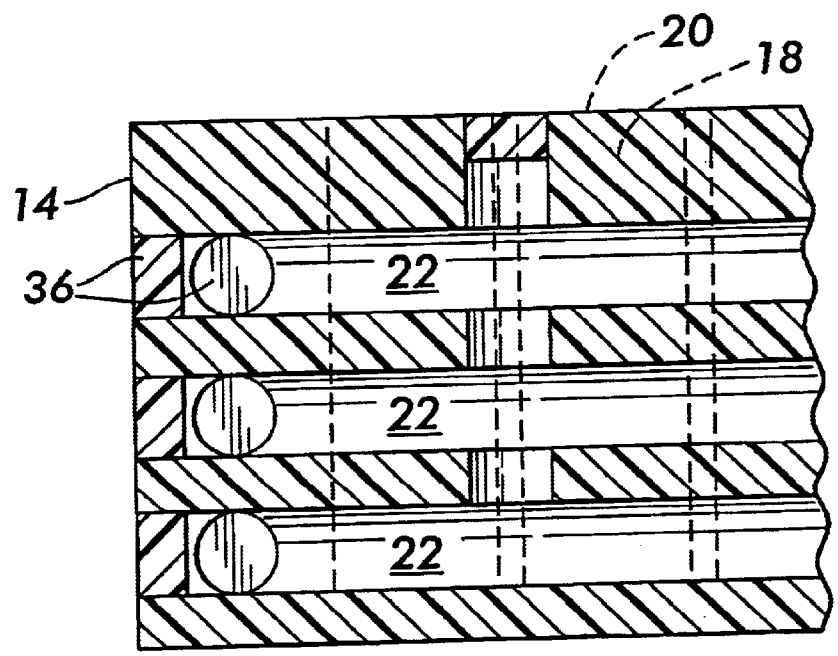
FIG. 7 is a partial cross-sectional view of an alternate embodiment of a multi-well plate according to the invention similar to FIG. 6.

While a single chamber 22 may be used per side of the plate as shown in FIG. 6, the invention contemplates using multiple chambers 22 arranged one above the other along one or more sides of a plate as shown in FIG. 7. This embodiment will allow more fluid to be positioned between a row of wells and a side portion 14 of the plate, thereby increasing the effectiveness of the chambers as a heat reservoir as described below.

Chambers 22, when filled with an appropriate substance 26, act as heat reservoirs to slow or prevent heat loss from the sides 14 to the cooler ambient air within the microwave oven. The substance acts as a buffer which does not allow significant heat transfer from wells 24 positioned adjacent to the sides, thus, allowing all of the wells to maintain substantially the same temperature and avoid any significant temperature gradient between wells at the center of the plate and wells nearer to the sides 14. By avoiding significant temperature gradients, the integrity of the experimental results will not be compromised and meaningful results will be obtained for all of the reactants in all of the wells of the multi-well plate according to the invention.

To ensure effective operation of the multi-well plate, it is preferred that a liquid within chambers 22 have a boiling point relatively higher than the temperature at which the experiment is to be run. This will ensure that the chambers remain fluid filled and continue to act as a heat reservoir to reduce or eliminate temperature gradients, and also do not form a vapor which may contaminate the atmosphere within the oven, possibly compromising the integrity of the experiment. Safety is also an issue since liquid, heated to its boiling point within a sealed chamber, may achieve significant pressure before the chamber bursts and spews the hot liquid and vapor into the oven.

For example, for an experiment designed to heat the samples within the wells to a constant temperature of about 130° C., the preferred liquid 26 within chambers 22 is N-methylpyrrolidinone, which has a boiling point of 202° C. at one atmosphere of pressure. A boiling point for the liquid substance 26 of at least 50° C. above the temperature of the experiment provides an adequate safety margin for most applications.

For a standard multi-well plate made of polytetrafluoroethylene having 96 wells and dimensions of 124×85×27 mm, it is found that about 7 mL of liquid is sufficient to form an effective heat reservoir around the plate and reduce the temperature gradients to relative insignificance. A greater volume of liquid is preferred however to provide even more effective gradient smoothing.

Figure 8:
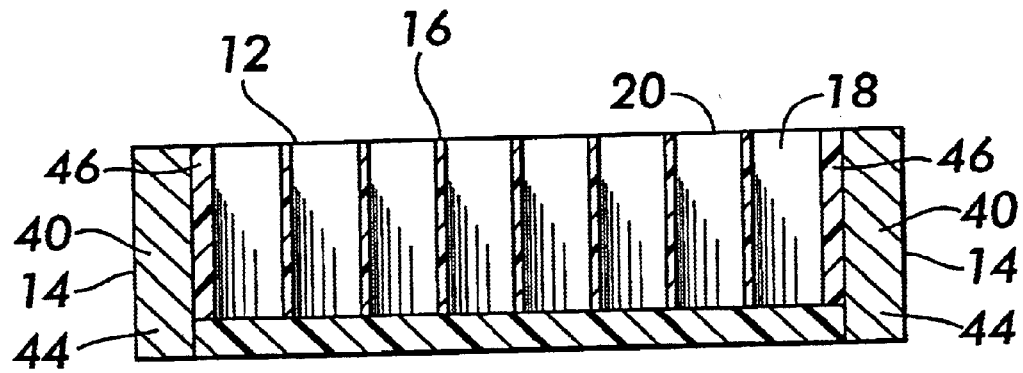
FIG. 8 is a cross-sectional view of another alternate embodiment of a multi-well plate according to the invention similar to FIG. 3.
Figure 9:
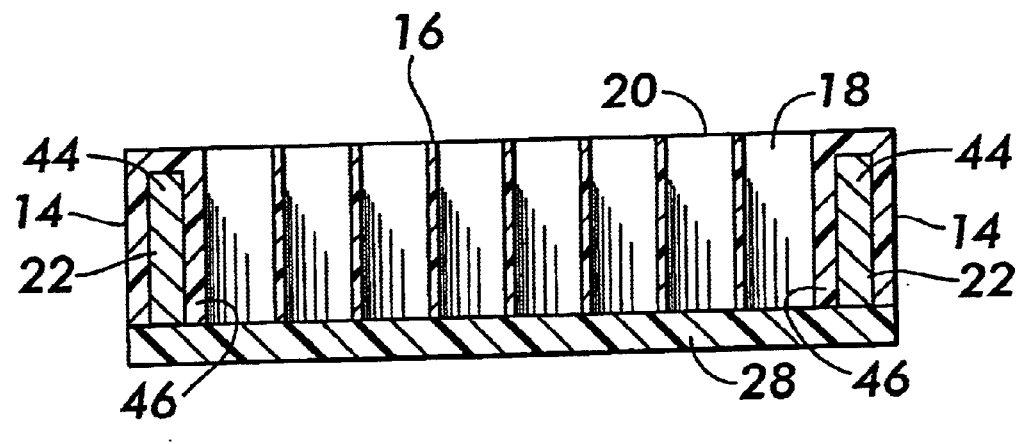
FIG. 9 is a cross-sectional view of another alternate embodiment of a multi-well plate according to the invention similar to FIG. 3.

In another embodiment, shown in FIG. 8, a heat reservoir 40 is formed around the planar member 12 by positioning an elongated body 44 of solid material lengthwise along the sides 46 directly adjacent to the wells 18. The elongated body 44 may be considered to form the side portions 14 and preferably extends continuously around the entire planar member. The material comprising body 44 is readily heatable by the microwave to the temperature of the experiment and thereby acts as a heat reservoir to prevent heat loss from the adjacent wells 18 to the cooler atmosphere within the microwave oven. The presence of the solid body surrounding the planar member 12 prevents any significant temperature gradients from forming between the center wells and the wells adjacent to the sides 46. Any gradients which would form would likely be confined to the elongated body 44 itself. The body 44 may be formed of ceramic material, as well as other solid materials. If the body 44 is a gelatinous material, it may be placed within the chamber 22 between the sides 46 and the side portion 14 as shown in FIG. 9 before the bottom plate 28 is attached to seal the chamber. This is similar to the embodiment shown in FIG. 3.

Figure 10:
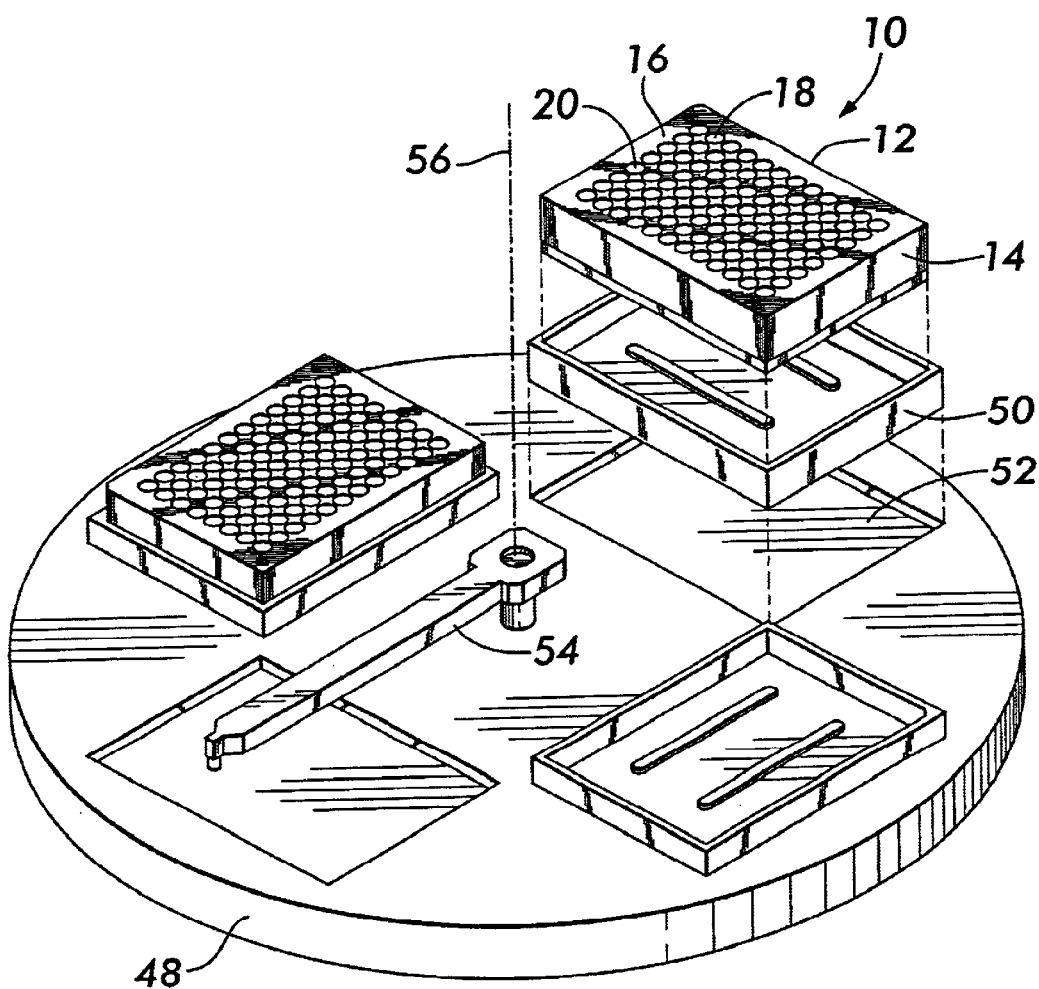
FIG. 10 is a perspective view of multi-well plates in use.

FIG. 10 shows multi-well plates 10 according to the invention being used on a turntable 48 which is positioned within a microwave oven, not shown. Preferably, the plates 10 resides in a tray 50 which is situated on turntable 48, preferably within a recess 52 to ensure proper positioning of the plate. A rotating arm 54 permits a measuring device, such as a thermometer, to be brought to bear on the plates to monitor the temperature of the compound samples in the wells. The turntable is powered and turns within the oven about vertical axis 56 to ensure even heating to all of the wells within all of the plates by the microwaves.

Experimental results achieved prove the effectiveness of the multi-well plate according to the invention when used in a microwave oven in chemical synthesis testing. For such a plate, 90% to 100% of the reactants in all wells go to product. This contrasts with multi-well plates according to the prior art wherein the reactants in the wells adjacent to the periphery see only 10% to 20% of the reactants going to product.

What is claimed is:

1. A multi-well plate for holding a compound for testing, said plate comprising:
    a substantially planar member bounded by downwardly depending side portions and having an upper surface;
    a plurality of wells positioned in said planar member and adapted to hold samples of said compound, each of said wells having an opening located on said upper surface, a first group of said wells being arranged adjacent to one of said side portions and a second group of said wells being arranged adjacent to another of said side portions;
    a first elongated chamber extending within said planar member lengthwise along said one side portion and confined between said one side portion and said first group of wells;
    a second elongated chamber extending within said planar member lengthwise along said other side portion and confined between said other side portion and said second group of wells, said first and second chambers being in fluid communication with one another, said first chamber being adapted to confine a fluid between said one side portion and said first group of wells, said second chamber being adapted to confine a fluid between said other side portion and said second group of wells, said fluid having the capacity to act as a heat reservoir and resist temperature changes of said samples in said first and second groups of wells relative to the samples in others of said wells.

2. A multi-well plate according to claim 1, wherein said planar member is made of a microwave transparent material.

3. A multi-well plate according to claim 2, wherein said material is polytetrafluoroethylene.

4. A multi-well plate according to claim 1, further comprising a port in said planar member in fluid communication with said first chamber, said port being adapted to receive said fluid for filling said first chamber therewith.

5. A multi-well plate according to claim 4, wherein said port is positioned on said upper surface.

6. A multi-well plate according to claim 1, wherein said chambers extends continuously around said planar member, said chambers being confined between said side portions and said wells positioned adjacent to said side portions.

7. A multi-well plate according to claim 1, wherein said fluid is a liquid.

8. A multi-well plate according to claim 7, wherein said liquid has a higher boiling point temperature than the temperature to which said compound will be heated.

9. A multi-well plate according to claim 8, wherein said liquid has a boiling point temperature at least about 50° C. higher than the temperature to which said compound will be heated.

10. A multi-well plate for holding a compound for testing, said plate comprising:
    a substantially planar member bounded by a plurality of downwardly depending side portions and having an upper surface;
    a plurality of wells positioned in said planar member and adapted to hold said samples of said compound, each of said wells having an opening located on said upper surface, a group of said wells being arranged adjacent to said side portions;
    an elongated chamber extending continuously around said planar member, said chamber being confined between said side portions and said wells adjacent to said side portions; and
    a fluid confined in said chamber between said side portions and said wells, said fluid having a capacity to act as a heat reservoir to resist temperature changes of said samples in said wells adjacent to said side portions relative to samples in others of said wells.

11. A multi-well plate according to claim 10, wherein said chamber is sealed and thereby isolated from the ambient.

12. A multi-well plate according to claim 11, wherein said fluid is a liquid.

13. A multi-well plate according to claim 12, wherein said fluid has a higher boiling point temperature than the temperature to which said sample compound is to be heated.

14. A multi-well plate according to claim 13, wherein said liquid has a boiling point temperature at least about 50° C. higher than the temperature to which said compound will be heated.

15. A multi-well plate for holding a compound for testing, said plate comprising:
    a substantially planar member having an upper surface and a plurality of side portions bounding said planar member;
    a plurality of wells positioned in said planar member and adapted to hold samples of said compound, each of said wells having an opening located on said upper surface, a first group of said wells being arranged adjacent to one of said side portions; and
    a first elongated body confined between said one side portion and said first group of said wells, said body comprising a solid material heatable by microwaves and having a capacity to act as a heat reservoir to resist temperature changes of said samples in said first group of wells relative to the samples in others of said wells.

16. A multi-well plate according to claims 15, wherein said planar member is made of a microwave transparent material.

17. A multi-well plate according to claim 15, wherein said body extends substantially continuously around said planar member.

18. A multi-well plate for holding a compound for testing, said plate comprising:
    a substantially planar member bounded by downwardly depending side portions and having an upper surface;

a plurality of wells positioned in said planar member and adapted to hold samples of said compound, each of said wells having an opening located on said upper surface, a group of said wells being arranged adjacent to said side portions; and an elongated chamber extending continuously around said planar member and confined between said side portions and said wells positioned adjacent to said side portions, said chamber being adapted to confine a fluid between said portions and said wells, said fluid having the capacity to act as a heat reservoir and resist temperature changes of said samples in said group of wells positioned adjacent to said side portions relative to the samples in others of said wells.

19. A multi-well plate according to claim 18, wherein said planar member is made of a microwave transparent material.

20. A multi-well plate according to claim 19, wherein said material is polytetrafluoroethylene.

21. A multi-well plate according to claim 18, further comprising a port in said planar member in fluid communication with said chamber, said port being adapted to receive said fluid for filling said chamber therewith.

22. A multi-well plate according to claim 21, wherein said port is positioned on said upper surface.

23. A multi-well plate according to claim 18, wherein said fluid is a liquid.

24. A multi-well plate according to claim 23, wherein said liquid has a higher boiling point temperature than the temperature to which said compound will be heated.

25. A multi-well plate according to claim 24, wherein said liquid has a boiling point temperature at least about 50° C. higher than the temperature to which said compound will be heated.

* * * * *